US006316692B1

(12) United States Patent
Readhead et al.

(10) Patent No.: US 6,316,692 B1
(45) Date of Patent: Nov. 13, 2001

(54) TRANSFECTION, STORAGE AND TRANSFER OF MALE GERM CELLS FOR GENERATION OF TRANSGENIC SPECIES AND GENETIC THERAPIES

(76) Inventors: Carol W. Readhead, 2185 San Pasqual St., Pasadena, CA (US) 91107; Robert Winston, 11 Denman Drive, London NW11 6RE (GB)

( * ) Notice: Subject to any disclaimer, the term of this patent is extended or adjusted under 35 U.S.C. 154(b) by 0 days.

(21) Appl. No.: 09/191,920

(22) Filed: Nov. 13, 1998

Related U.S. Application Data

(60) Provisional application No. 60/065,825, filed on Nov. 14, 1997.

(51) Int. Cl.[7] .......................... C12N 15/09; C12N 15/00; C12N 15/63; A01N 43/04; A61K 31/70

(52) U.S. Cl. ................................ 800/14; 800/21; 800/22; 800/25; 800/3; 435/455; 435/320.1; 435/325; 514/44

(58) Field of Search ................................ 800/21, 22, 25, 800/14, 3; 514/44; 435/455, 320.1, 325

(56) References Cited

U.S. PATENT DOCUMENTS

| | | | |
|---|---|---|---|
| 4,870,009 | 9/1989 | Evans et al. | 435/70 |
| 5,175,384 | 12/1992 | Krimpenfort et al. | 800/18 |
| 5,434,340 | 7/1995 | Krimpenfort et al. | 800/18 |
| 5,521,291 | 5/1996 | Curiel et al. | 530/391.7 |
| 5,547,932 | 8/1996 | Curiel et al. | 435/65 |
| 5,591,669 | 1/1997 | Krimpenfort et al. | 800/18 |

FOREIGN PATENT DOCUMENTS

| | | |
|---|---|---|
| 0 867 114 A1 | 9/1998 | (EP) . |
| WO 90/08192 | 7/1990 | (WO) . |
| WO 92/03459 | 3/1992 | (WO) . |
| WO 93/11228 | 6/1993 | (WO) . |
| WO 95/02041 | 1/1995 | (WO) . |

OTHER PUBLICATIONS

Chang et al. Production of Transgenic Rats and Mice by the Testis–Mediated Gene Transfer. Journal of Reproduction and Development, vol. 45, No. 1, pp. 29–36, 1999.*

Eck et al. Gene–Based Therapy, Goodman & Gilman's The Pharmacological Basis of Therapeutics, 9th edition, chapter 5, 1996.*

Verma et al. Gene Therapy—Promises, Problems, and Prospects. Nature, vol. 389, pp. 239–242, Sep. 18, 1997.*

Saito et al., Direct injection of foreign DNA into mouse testis as a possible alternative of sperm–mediated gene transfer, Animal Biotechnology, vol. 5, pp. 19–31, 1994.*

Powers et al., "Electroporation as an effective means of introducing DNA into abalone (*Haliotis rufescens*) embryos," *Molecular Marine Biology and Biotechnology* 4(4):360–375 (1995).

Müller et al., "Efficient transient expression system based on square pulse electroporation and in vivo luciferase assay of fertilized fish eggs," *Federation of European Biochemical Societies* 324(1):27–32 (1993).

Leopold et al., "Using electroporation and a slot curvette to deliver plasmid DNA to insect embryos," *Genetic Analysis: Biomolecular Engineering* 12:197–200 (1996).

Nemec et al., "Introduction of DNA into murine embryos by electroporation," Annual Conference of the International Embryo Transfer Society Theriogenology Jan. 15–17, 1989.

XP–002099974, JO9220039, "Introducing Extraneous Gene Sperm Ovum Produce Transgenic Animal Comprise Introducing Extraneous Gene Liposome Complex Through Testicular Ovary Artery Sperm Testicular Ovum Ovary", Abstract Only.

Brinster, et al., No Simple Solution for Making Transgenic Mice, *Cell,* vol. 59, pp. 239–241, Oct. 20, 1989.

Naito, M. et al., "Donor primordial germ cell–derived offspring from recipient germline chickens: absence of long term immune rejection and effects on sex rations," British Poultry Science, vol. 39, pp. 20–23 (1998).

Avarbock, Mary R., et al., Reconstitution of spermatogenesis from frozen spermatogonial stem cells, *Nature Medicine,* vol. 2, No. 6, pp. 693–696, (Jun., 1996).

Birnstiel, Max L. et al., Dangerous Liasons: Spermatozoa as Natural Vectors for Foreign DNA?, *Cell,* vol. 57, pp. 701–702, (1989).

Blanchard, K.. T. et al., Adenovirus–mediated gene transfer to rat testis in vivio, Biol Reprod (Feb. 1997); 56(2):495–500.

Brinster, Ralph L. et al., Avarbock, Germline transmission of donor haplotype following spermatogonial transplantation, *Proc. Natl. Acad. Sci. USA,* vol. 91 pp. 22303–22307, (Nov. 1994) Developmental Biology.

Brinster, Ralph L. et al., Spermatogenesis following male germ–cell transplantation, *Proc. Natl. Acad. Sci. USA,* Vo. 91, pp. 11298–11302, (Nov. 1994), Developmental Biology.

Clouthier, D. E. et al., Rat spermatogenesis in mouse testis, *Nature,* 381 (6581):418–421 (May 30, 1996).

(List continued on next page.)

*Primary Examiner*—Jill D. Martin
(74) *Attorney, Agent, or Firm*—Sidley Austin Brown & Wood

(57) ABSTRACT

A composition for in vivo transfection of non-human mammalian male germ cells comprises a nucleic acid or transgene, and a gene delivery system, and optionally a protective internalizing agent, such as an endosomal lytic agent, a virus or a viral component, which is internalized by cells along with the transgene and which enhances gene transfer through the cytoplasm to the nucleus of the male germ cell. A pharmaceutical preparation and a transfer kit utilize the composition. A method for introducing a polynucleotide into non-human mammalian male germ cells comprises the administration of the composition to a non-human mammalian. A method for isolating or selecting transfected cells utilizes a reporter gene, and a method for administering transfected male germ cells utilizes male germ cells which have been transfected in vitro.

25 Claims, No Drawings

OTHER PUBLICATIONS

Curiel D. T., et al. Adenovirus enhancement of transferrin-polylysine–mediated gene delivery, *Proc. Natl. Acad. Sci.–USA,* 88:8850–54 (Oct. 1991).

Gabarek & Gergely, Zero–length cross–linking procedure with the use of active esters, *Analyt. Biochem* 185: 131–135 (1990).

Hovatta, Outi, et al., Cryopreservation of human ovarian tissue using dimethylsulphoxide and propanediol–sucrose as cryoprotectants, *Human Reproduction,* vol. 11, No. 6, pp. 1268–1272, (1996).

Hovatta, Outi, et al., Pregnancy resulting from intracytoplasmic injection of spermatozoa from a frozen–thawed testicular biopsy specimen, *Human Reproduction,* vol. 11, No. 11, pp. 2472–2473, (1996).

Jiang, F–X et al., Male germ cell transplantation in rats: aparent synchronization of spermatogenesis between host and donor seminiferous epithelia, International Journal of Andrology, vol. 18, pp. 326–330 (1995).

Jiang, Fang–Xu et al., Different fate of primordial germ cells and gonocytes following transplantation, *APMIS,* vol. 106, pp. 58–63, (1998).

Johnson L, et al., Heterotoic transplantation as a model to study the regulation of spermatogenesis; some histomorphological considerations about sperm decline in man; *Contracept Fertil Sex* 1997 vol. 25(7–8), pp. 549–555, (1997).

Jones and Shenk, An adenovirus type 5 early gene function regulates expression of other early viral genes, *Proc. Natl. Acad. Sci. USA,* 76:(8)3665–3669 (1979).

Kim, J. H. et al., Development of a positive method for male stem cell–mediated gene transfer in mouse and pig; *Mol Reprod Dev,* Apr;46(4):515–526 (1997).

Kim, V. Narry et al., Minimal requirement for a Lentivirus Vector Based on Human Immunodeficiency Virus Type 1, *Journal of Virology,* pp. 811–816, (Jan. 1988).

Lavitrano, Mariauisa et al., Sperm Cells as Vectors for Introducing Foreign DNA Into Eggs: Genetic Transformation of Mice, *Cell,* vol. 57, pp. 717–723, (Jun. 2, 1989).

Mittereder et al., Evaluation of the concentration and bioactivity of adenovirus vectors for gene therapy, *J. Virology,* 70:7498–7509 (1996).

Muramatsu T. et al., Foreign gene expression in the mouse testis by localized in vivo gene transfer, *Biochem Biophys Res Commun,* 7;233(1):45–49 (Apr. 1997).

Nagano, M. et al., Spermatogonial transplantation and reconstitution of donor cell spermatogenesis in recipient mice, *APMIS,* vol. 106, pp. 47–57, (1998).

Naito M. et al., Production of germline chimeric chickens, with high transmission rate of donor–derived gametes, produced by transfer of primordial germ cells, *Molecular Reprod Dev.,* 39(2):153–161(Oct. 1994).

Ogawa, Takehiko et al., Transplantation of testis germinal cells into mouse seminiferous tubules, *Int. J. Dev. Biol.,* 41:222–122 (1997).

Ono T. et al., Transfer of male or female primordial germ cells of quail into chick embryonic gonads, *Exp. Anim,* 45(4):347–352 (Oct. 1996).

Perez–Cruet, M. J., et al., Adenovirus–Mediated Gene Therapy of Experimental gliomas, *Journal of Neuroscience Research,* vol. 39, pp. 506–511(1994).

Russell, L. D. et al., Ultrastructural observations of spermatogenesis in mice resulting from transplantation of mouse spermatogonia, *J. Androl,* 17(6):603–614 (Nov. 1996).

Schmidt, Jerzy A. et al., Control of Erythroid Differentiation. Possible Role of the Transferrin cycle, *Cell,* vol. 46, 41–51 (Jul. 4, 1986).

Schiedner, Gudrun et al., Genomic DNA transfer with a high–capacity adenovirus vector results in improved in vivo gene expression and decreased toxicity, *Nature Genetics,* vol. 18, pp. 180–183, Feb. 1998.

Wagner, Ernst et al., Transferrin–polycation conjugates as carriers for DNA uptake into cells, *Proc. Natl. Academy. Sci. USA,* vol. 87, pp. 3410–3414 (May 1990).

Baranov, V. S., et al., The possibility of the incorporation of macromolecules, including exogenous DNA, into the germ cells of male mice. The liposome method and Ca–P coprecipitation method,, *Tsitol Genet,* vol. 24, (2), pp. 52–55, (1990) (Abstract only).

Chen, Shu–Hsia et al., Gene therapy for brain tumors: Regression of experimental gliomas by adenovirus–mediated gene transfer invivo, *Proc. Natl., Acad. Sci. Usa,* vol. 91, pp. 3054–3057 (Apr. 1994).

* cited by examiner

TRANSFECTION, STORAGE AND TRANSFER OF MALE GERM CELLS FOR GENERATION OF TRANSGENIC SPECIES AND GENETIC THERAPIES

This application claims the benefit of U.S. Provisional Application No. 60/065825, filed on Nov. 14, 1997.

BACKGROUND OF THE INVENTION

1. Field of the Invention

The present invention relates to the field of transgenics and gene therapy. More specifically, this invention relates to in vitro and in vivo methods for transfecting germ cells and, in some instances, incorporating a nucleic acid segment encoding a specific trait into the male germ cells of an animal. When the nucleic acid becomes incorporated into the germ cell genome, upon mating, or in vitro fertilization and the like, the trait may be transmitted to the progeny. The present technology is suitable for breeding progeny with or without a desired trait by modifying their genome. This technology is also suitable for use in introducing a therapeutic gene into the germ or support cells (e.g., Leydig and Sertoli cells) of the testis and is, therefore, suitable for use in gene therapy for males with fertility problems associated with genetic defects.

2. Description of the Background

The field of transgenics was initially developed to understand the action of a single gene in the context of the whole animal and phenomena of gene activation, expression, and interaction. This technology has been used to produce models for various diseases in humans and other animals. Transgenic technology is amongst the most powerful tools available for the study of genetics, and the understanding of genetic mechanisms and function. It is also used to study the relationship between genes and diseases. About 5,000 diseases are caused by a single genetic defect. More commonly, other diseases are the result of complex interactions between one or more genes and environmental agents, such as viruses or carcinogens. The understanding of such interactions is of prime importance for the development of therapies, such gene therapy and drug therapies, and also treatments such as organ transplantation. Such treatments compensate for functional deficiencies and/or may eliminate undesirable functions expressed in an organism. Transgenesis has also been used for the improvement of livestock, and for the large scale production of biologically active pharmaceuticals.

Historically, transgenic animals have been produced almost exclusively by micro injection of the fertilized egg. The pronuclei of fertilized eggs are micro injected in vitro with foreign, i.e. xenogeneic or allogeneic DNA or hybrid DNA molecules. The micro injected fertilized eggs are then transferred to the genital tract of a pseudopregnant female. The generation of transgenic animals by this technique is generally reproducible, and for this reason little has been done to improve on it. This technique, however, requires large numbers of fertilized eggs. This is partly because there is a high rate of egg loss due to lysis during micro injection. Moreover manipulated embryos are less likely to implant and survive in utero. These factors contribute to the technique's extremely low efficiency. For example, 300–500 fertilized eggs may need to be micro injected to produce perhaps three transgenic animals. Partly because of the need to micro inject large numbers of embryos, transgenic technology has largely been exploited in mice because of their high fecundity. Whilst small animals such as mice have proved to be suitable models for certain diseases, their value in this respect is limited. Larger animals would be much more suitable to study the effects and treatment of most human diseases because of their greater similarity to humans in many aspects, and also the size of their organs. Now that transgenic animals with the potential for human xenotransplantation are being developed, larger animals, of a size comparable to man will be required. Transgenic technology will allow that such donor animals will be immunocompatible with the human recipient. Historical transgenic techniques, however, require that there be an ample supply of fertilized female germ cells or eggs. Most large mammals, such as primates, cows, horses and pigs produce only 10–20 or less eggs per animal per cycle even after hormonal stimulation. Consequently, generating large animals with these techniques is prohibitively expensive.

This invention relies on the fact that vast numbers of male germ cells are more readily available. Most male mammals generally produce at least $10^8$ spermatozoa (male germ cells) in each ejaculate. This is in contrast to only 10–20 eggs in a mouse even after treatment with superovulatory drugs. A similar situation is true for ovulation in nearly all larger animals. For this reason alone, male germ cells will be a better target for introducing foreign DNA into the germ line, leading to the generation of transgenic animals with increased efficiency and after simple, natural mating.

Initially, attempts were made to produce transgenic animals by adding DNA to spermatozoa which were then used to fertilize mouse eggs in vitro. The fertilized eggs were then transferred to pseudopregnant foster females, and of the pups born, 30% were reported to be transgenic and express the transgene. Despite repeated efforts by others, however, this experiment could not be reproduced and no transgenic pups were obtained. Indeed, there remains little doubt that the transgenic animals reputed to have been obtained by this method were not transgenic at all and the DNA incorporation reported was mere experimental artifact. Data collected from laboratories around the world engaged in testing this method showed that no transgenics were obtained from a total of 890 pups generated.

In summary, it is currently possible to produce live transgenic progeny but the available methods are costly and extremely inefficient. Spermatogenic transfection in accordance with this invention, either in vitro or in vivo, provides a simple, less costly and less invasive method of producing transgenic animals and one that is potentially highly effective in transferring allogeneic as well as xenogeneic genes into the animal's germ cells. The present technology is also of great value in producing transgenic animals in large species as well as for repairing genetic defects which lead to male infertility. The present technology is also suitable for germ line gene therapy in humans and other animal species. Male germ cells that have stably integrated the DNA could be selected.

SUMMARY OF THE INVENTION

The present invention relates to the in vivo and ex vivo (in vitro) transfection of eukaryotic animal germ cells with a desired genetic material. Briefly, the in vivo method involves injection of genetic material together with a suitable vector directly into the testicle of the animal. In this method, all or some of the male germ cells within the testicle are transfected in situ, under effective conditions. The ex vivo method involves extracting germ cells from the gonad of a suitable donor or from the animal's own gonad, using a novel isolation method, transfecting them in vitro, and then returning them to the testis under suitable conditions where they will spontaneously repopulate it. The ex vivo method has the advantage that the transfected germ cells may be screened by various means before being returned to the testis to ensure that the transgene is incorporated into the genome in a stable state. Moreover, after screening and cell sorting only enriched populations of germ cells may be returned. This approach provides a greater chance of transgenic progeny after mating.

This invention also relates to a novel method for the isolation of spermatogonia, comprising obtaining spermatogonia from a mixed population of testicular cells by extruding the cells from the seminiferous tubules and gentle enzymatic disaggregation. The spermatogonia or stem cells which are to be genetically modified, may be isolated from a mixed cell population by a novel method including the utilization of a promoter sequence, which is only active in cycling spermatogonia stem cell populations, for example, b-Myb or a spermotogonia specific promoter, such as the c-kit promoter region, c-raf-1 promoter, ATM (ataxia-telangiectasia) promoter, RBM (ribosome binding motif) promoter, DAZ (deleted in azoospermia) promoter, XRCC-1 promoter, HSP 90 (heat shock gene) promoter, or FRMI (from fragile X site) promoter, optionally linked to a reporter construct, for example, the Green Fluorescent Protein Gene (EGFP). These unique promoter sequences drive the expression of the reporter construct only in the cycling spermatogonia. The spermatogonia, thus, are the only cells in the mixed population which will express the reporter construct and they, thus, may be isolated on this basis. In the case of the green fluorescent reporter construct, the cells may be sorted with the aid of, for example, a FACs scanner set at the appropriate wavelength or they may be selected by chemical methods.

This invention also relates to the repopulation of a testis with germ cells that have been isolated from a fresh or frozen testicular biopsy. These germ cells may or may not be genetically manipulated prior to reimplantation.

For transfection, the method of the invention comprises administering to the animal, or to germ cells in vitro, a composition comprising amounts of nucleic acid comprising polynucleotides encoding a desired trait. In addition, the composition comprises, for example, a relevant controlling promoter region made up of nucleotide sequences. This is combined with, for example, a gene delivery system comprising a cell transfection promotion agent such as retro viral vectors, adenoviral and adenoviral related vectors, or liposomal reagents or other agents used for gene therapy. These introduced under conditions effective to deliver the nucleic acid segments to the animal's germ cells optionally with the polynucleotide inserted into the genome of the germ cells. Following incorporation of the DNA, the treated animal is either allowed to breed naturally, or reproduced with the aid of assisted reproductive technologies, and the progeny selected for the desired trait.

This technology is applicable to the production of transgenic animals for use as animal models, and to the modification of the genome of an animal, including a human, by addition, modification, or subtraction of genetic material, often resulting in phenotypic changes. The present methods are also applicable to altering the carrier status of an animal, including a human, where that individual is carrying a gene for a recessive or dominant gene disorder, or where the individual is prone to pass a multigenic disorder to his offspring.

A preparation suitable for use with the present methods comprises a polynucleotide segment encoding a desired trait and a transfection promotion agent, and optionally an uptake promotion agent which is sometime equipped with agents protective against DNA breakdown. The different components of the transfection composition are also provided in the form of a kit, with the components described above in measured form in two or more separate containers. The kit generally contains the different components in separate containers. Other components may also be provided in the kit as well as a carrier.

DESCRIPTION OF THE PREFERRED EMBODIMENTS

The present invention arose from a desire by the present inventors to improve on existing methods for the genetic modification of an animal's germ cells and for producing transgenic animals. The pre-existing art methods rely on direct injection of DNA into zygotes produced in vitro or in vivo, or by the Production of chimeric embryos using embryonal stem cells incorporated into a recipient blastocyst. Following this, such treated embryos are transferred to the primed uterus or oviduct. The available methods are extremely slow and costly, rely on several invasive steps, and only produce transgenic progeny sporadically and unpredictably.

In their search for a less costly, faster, and more efficient approach for producing transgenics, the present inventors devised the present method which relies on the in vivo or ex vivo (in vitro) transfection of male animal germ cells with a nucleic acid segment encoding a desired trait. The present method relies on at least one of the following strategies. A first method delivers the nucleic acid segment using known gene delivery systems in situ to the gonad of the animal (in vivo transfection), allows the transfected germ cells to differentiate in their own milieu, and then selects for animals exhibiting the nucleic acid's integration into its germ cells (transgenic animals). The thus selected animals may be mated, or their sperm utilized for insemination or in vitro fertilization to produce transgenic progeny. The selection may take place after biopsy of one or both gonads, or after examination of the animal's ejaculate amplified by the polymerase chain reaction to confirm the incorporation of the desired nucleic acid sequence. In order to simplify the confirmation of the actual incorporation of the desired nucleic acid, the initial transfection may include a co-transfected reporter gene, such as a gene encoding for Green Fluorescent Protein, which fluoresces under suitable wave-lengths of ultra-violet light.

Alternatively, male germ cells may be isolated from a donor animal and transfected, or genetically altered in vitro to impart the desired trait. Following this genetic manipulation, germ cells which exhibit any evidence that the DNA has been modified in the desired manner are selected, and transferred to the testis of a suitable recipient animal. Further selection may be attempted after biopsy of one or both gonads, or after examination of the animal's ejaculate amplified by the polymerase chain reaction to confirm whether the desired nucleic acid sequence was actually incorporated. As described above, the initial transfection may have included a co-transfected reporter gene, such as a gene encoding the Green Fluorescent Protein. Before transfer of the germ cells, the recipient testis are generally treated in one, or a combination, of a number of ways to inactivate or destroy endogenous germ cells, including by gamma irradiation, by chemical treatment, by means of infectious agents such as viruses, or by autoimmune depletion or by combinations thereof. This treatment facilitates the colonization of the recipient testis by the altered donor cells.

Animals that were shown to carry suitably modified sperm cells then may be either allowed to mate naturally, or alternatively their spermatozoa are used for insemination or in vitro fertilization. The thus obtained transgenic progeny may be bred, whether by natural mating or artificial insemination, to obtain further transgenic progeny. The method of this invention has a lesser number of invasive procedures than other available methods, and a high rate of success in producing incorporation into the progeny's genome of the nucleic acid sequence encoding a desired trait.

Primordial germ cells are thought to arise from the embryonic ectoderm, and are first seen in the epithelium of the endodermal yolk sac at the E8 stage. From there they migrate through the hindgut endoderm to the genital ridges. The primitive spermatogonial stem cells, known as A0/As, differentiate into type B spermatogonia. The latter further differentiate to form primary sperrnatocytes, and enter a prolonged meiotic prophase during which homologous chromosomes pair and recombine. Several morphological stages of meiosis are distinguishable: preleptotene, leptotene, zygotene, pachytene, secondary spermatocytes, and the haploid spermatids. The latter undergo further morphological changes during spermatogenesis, including the reshaping of their nucleus, the formation of acrosome, and assembly of the tail. The final changes in the spermatozoon take place in the genital tract of the female, prior to fertilization. The uptake of the nucleic acid segment administered by the present in vivo method to the gonads will reach germ cells that are at one or more of these stages, and be taken up by those that are at a more receptive stage. In the ex vivo (in vitro) method of genetic modification, generally only diploid spermatogonia are used for nucleic acid modification. The cells may be modified in vivo using gene therapy techniques, or in vitro using a number of different transfection strategies.

The inventors are, thus, providing in this patent a novel and unobvious method for; isolation of male germ cells, and for the in vivo and ex vivo (in vitro) transfection of allogeneic as well as xenogeneic DNA into an animal's germ cells. This comprises the administration to an animal of a composition comprising a gene delivery system and at least one nucleic acid segment, in amounts and under conditions effective to modify the animal's germ cells, and allowing the nucleic acid segment to enter, and be released into, the germ cells, and to integrate into their genome.

The in vivo introduction of the gene delivery mixture to the germ cells may be accomplished by direct delivery into the animal's testis (es), where it is distributed to male germ cells at various stages of development. The in vivo method utilizes novel technology, such as injecting the gene delivery mixture either into the vasa efferentia, directly into the seminiferous tubules, or into the rete testis using, for example, a micropipette. To ensure a steady infusion of the gene delivery mixture, under pressures which will not damage the delicate tubule system in the testis, the injection may be made through the micropipette with the aid of a picopump delivering a precise measured volume under controlled amounts of pressure. The micropipette may be made of a suitable material, such as metal or glass, and is usually made from glass tubing which has been drawn to a fine bore at its working tip, e.g. using a pipette puller. The tip may be angulated in a convenient manner to facilitate its entry into the testicular tubule system. The micropipette may be also provided with a beveled working end to allow a better and less damaging penetration of the fine tubules at the injection site. This bevel may be produced by means of a specially manufactured grinding apparatus. The diameter of the tip of the pipette for the in vivo method of injection may be about 15 to 45 microns, although other sizes may be utilized as needed, depending on the animal's size. The tip of the pipette may be introduced into the rete testis or the tubule system of the testicle, with the aid of a binocular microscope with coaxial illumination, with care taken not to damage the wall of the tubule opposite the injection point, and keeping trauma to a minimum. On average, a magnification of about ×25 to ×80 is suitable, and bench mounted micromanipulators are not severally required as the procedure may be carried out by a skilled artisan without additional aids. A small amount of a suitable, non-toxic dye, may be added to the gene delivery fluid to confirm delivery and dissemination to the tubules of the testis. It may include a dilute solution of a suitable, non-toxic dye, which may be visualized and tracked under the microscope.

In this manner, the gene delivery mixture is brought into intimate contact with the germ cells. The gene delivery mixture typically comprises the modified nucleic acid encoding the desired trait, together with a suitable promoter sequence, and optionally agents which increase the uptake of the nucleic acid sequence, such as liposomes, retroviral vectors, adenoviral vectors, adenovirus enhanced gene delivery systems, or combinations thereof A reporter construct such as the gene encoding for Green Fluorescent Protein may further be added to the gene delivery mixture. Targeting molecules such as c-kit ligand may be added to the gene delivery mixture to enhance the transfer of the male germ cell.

For the ex vivo (in vitro) method of genetic alteration, the introduction of the modified germ cells into the recipient testis may be accomplished by direct injection using a suitable micropipette. Support cells, such as Leydig or Sertoli cells that provide hormonal stimulus to spermatogonial differentiation, may be transferred to a recipient testis along with the modified germ cells. These transferred support cells may be unmodified, or, alternatively, may themselves have been transfected, together with- or separately from the germ cells. These transferred support cells may be autologous or heterologous to either the donor or recipient testis. A preferred concentration of cells in the transfer fluid may easily be established by simple experimentation, but will likely be within the range of about $1\times10^5$–$10\times10^5$ cells per 10 $\mu$l of fluid. This micropipette may be introduced into the vasa efferentia, the rete testis or the seminiferous tubules, optionally with the aid of a picopump to control pressure and/or volume, or this delivery may be done manually. The micropipette employed is in most respects similar to that used for the in vivo injection, except that its tip diameter generally will be about 70 microns. The microsurgical method of introduction is similar in all respects to that used for the in vivo method described above. A suitable dyestuff may also be incorporated into the carrier fluid for easy identification of satisfactory delivery of the transfected germ cells.

Once in contact with germ cells, whether they are in situ in the animal or vitro, the gene delivery mixture facilitates the uptake and transport of the xenogeneic genetic material into the appropriate cell location for integration into the genome and expression. A number of known gene delivery methods may be used for the uptake of nucleic acid sequences into the cell.

"Gene delivery (or transfection) mixture", in the context of this patent, means selected genetic material together with an appropriate vector mixed, for example, with an effective amount of lipid transfecting agent. The amount of each component of the mixture is chosen so that the transfection of a specific species of germ cell is optimized. Such optimization requires no more than routine experimentation. The ratio of DNA to lipid is broad, preferably about 1: 1, although other proportions may also be utilized depending on the type of lipid agent and the DNA utilized. This proportion is not crucial.

"Transfecting agent", as utilized herein, means a composition of matter added to the genetic material for enhancing the uptake of exogenous DNA segment(s) into a eukaryotic cell, preferably a mammalian cell, and more preferably a mammalian germ cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes may be targeted to the male germ cells using specific ligands which are recognized by receptors on the cell surface of the germ cell, such as the c-kit ligand or modifications thereof.

"Virus", as used herein, means any virus, or transfecting fragment thereof, which may facilitate the delivery of the genetic material into male germ cells. Examples of viruses which are suitable for use herein are adenoviruses, adeno-associated viruses, retroviruses such as human immune-deficiency virus, lentiviruses, such as Moloney murine leukemia virus and the retrovirus vector derived from Moloney virus called vesicular-stomatitis-virus-glycoprotein (VSV-G)-Moloney murine leukemia virus, mumps virus, and transfecting fragments of any of these viruses, and other viral DNA segments that facilitate the uptake of the desired DNA segment by, and release into, the cytoplasm of germ cells and mixtures thereof. The mumps virus is particularly suited because of its affinity for immature sperm cells including spermatogonia. All of the above viruses may require modification to render them non-pathogenic or less antigenic. Other known vector systems, however, may also be utilized within the confines of the invention.

"Genetic material", as used herein, means DNA sequences capable of imparting novel genetic modification (s), or biologically functional characteristic(s) to the recipient animal. The novel genetic modification(s) or characteristic(s) may be encoded by one or more genes or gene segments, or may be caused by removal or mutation of one or more genes, and may additionally contain regulatory sequences. The transfected genetic material is preferably functional, that is it expresses a desired trait by means of a product or by suppressing the production of another. Examples of other mechanisms by which a gene's function may be expressed are genomic imprinting, i.e. inactivation of one of a pair of genes (alleles) during very early embryonic development, or inactivation of genetic material by mutation or deletion of gene sequences, or by expression of a dominant negative gene product, among others.

In addition, novel genetic modification(s) may be artificially induced mutations or variations, or natural allelic mutations or variations of a gene(s). Mutations or variations may be induced artificially by a number of techniques, all of which are well known in the art, including chemical treatment, gamma irradiation treatment, ultraviolet radiation treatment, ultraviolet radiation, and the like. Chemicals useful for the induction of mutations or variations include carcinogens such as ethidium bromide and others known in the art.

DNA segments of specific sequences may also be constructed to thereby incorporate any desired mutation or variation or to disrupt a gene or to alter genomic DNA. Those skilled in the art will readily appreciate that the genetic material is inheritable and is, therefore, present in almost every cell of future generations of the progeny, including the germ cells.

Among novel characteristics are the expression of a previously unexpressed trait, augmentation or reduction of an expressed trait, over expression or under expression of a trait, ectopic expression, that is expression of a trait in tissues where it normally would not be expressed, or the attenuation or elimination of a previously expressed trait. Other novel characteristics include the qualitative change of an expressed trait, for example, to palliate or alleviate, or otherwise prevent expression of an inheritable disorder with a multigenic basis.

The method of the invention is suitable for application to a variety of vertebrate animals, all of which are capable of producing gametes, i.e. sperm or ova. Thus, in accordance with the invention novel genetic modification(s) and/or characteristic(s) may be imparted to animals, including mammals, such as humans, non-human primates, for example simians, marmosets, domestic agricultural animals such as sheep, cows, pigs, horses, particularly race horses, marine mammals, feral animals, rodents such as mice and rats, and the like. Other animals include fowl such as chickens, turkeys, ducks, ostriches, geese, rare and ornamental birds, and the like. Of particular interest are endangered species of wild animal, such rhinoceros, tigers, cheetahs, certain species of condor, and the like.

Broadly speaking, a "transgenic" animal is one that has had foreign DNA permanently introduced into its cells. The foreign gene(s) which (have) been introduced into the animal's cells is (are) called a "transgene(s)". The present invention is applicable to the production of transgenic animals containing xenogeneic, i.e., exogenous, transgenic genetic material, or material from a different species, including biologically functional genetic material, in its native, undisturbed form in which it is present in the animal's germ cells. In other instances, the genetic material is "allogeneic" genetic material, obtained from different strains of the same species, for example, from animals having a "normal" form of a gene, or a desirable allele thereof. Also the gene may be a hybrid construct consisting of promoter DNA sequences and DNA coding sequences linked together. These sequences may be obtained from different species or DNA sequences from the same species that are not normally juxtaposed. The DNA construct may also contain DNA sequences from prokaryotic organisms, such as bacteria, or viruses.

In one preferred embodiment, the transfected germ cells of the transgenic animal have the non-endogenous (exogenous) genetic material integrated into their chromosomes. This is what is referred to as a "stable transfection". This is applicable to all vertebrate animals, including humans. Those skilled in the art will readily appreciate that any desired traits generated as a result of changes to the genetic material of any transgenic animal produced by this invention are inheritable. Although the genetic material was originally inserted solely into the germ cells of a parent animal, it will ultimately be present in the germ cells of future progeny and subsequent generations thereof. The genetic material is also present in the differentiated cells, i.e. somatic cells, of the progeny. This invention also encompasses progeny resulting from breeding of the present transgenic animals. The transgenic animals bred with other transgenic or non-transgenic animals of the same species will produce some transgenic progeny, which should be fertile. This invention, thus, provides animal line(s) which result from breeding of the transgenic animal(s) provided herein, as well as from breeding their fertile progeny.

"Breeding", in the context ofthis patent, means the union of male and female gametes so that fertilization occurs. Such a union may be brought about by natural mating, i.e. copulation, or by in vitro or in vivo artificial means. Artificial means include, but are not limited to, artificial insemination, in vitro fertilization, cloning and embryo transfer, intracytoplasmic spermatozoal microinjection, cloning and embryo splitting, and the like. However, others may also be employed.

The transfection of mature male germ cells may be also attained utilizing the present technology upon isolation of the cells from a vertebrate, as is known in the art, and exemplified in Example 10. The thus isolated cells may then be transfected ex vivo (in vitro), or cryopreserved as is known in the art and exemplified in Example 11. The actual transsection of the isolated testicular cells may be accomplished, for example, by isolation of a vertebrate's testes, decapsulation and teasing apart and mincing of the seminiferous tubules. The separated cells may then be incubated in an enzyme mixture comprising enzymes known for gently breaking up the tissue matrix and releasing undamaged cells such as, for example, pancreatic trypsin, collagenase type I, pancreatic DNAse type I, as well as bovine serum albumin and a modified DMEM medium. The cells may be incubated in the enzyme mixture for a period of about 5 min to about 30 min, more preferably about 15 to about 20 min, at a temperature of about 33° C. to about 37° C., more preferably about 36 to 37° C. After washing the cells free of the enzyme mixture, they may be placed in an incubation medium such as DMEM, and the like, and plated on a culture dish. Any of a number of commercially available transfection mixtures may be admixed with the polynucleotide encoding a desire trait or product for transfection of the cells. The transfection mixture may then be admixed with the cells and allowed to interact for a period of about 2 hrs to about 16 hrs, preferably about 3 to 4 hrs, at a temperature of about 33° C. to about 37° C., preferably about 36° C. to 37° C., and more preferably in a constant and/or controlled atmosphere. After this period, the cells are preferably placed at a lower temperature of about 33° C. to about 34° C., preferably about 30–35° C. for a period of about 4 hrs to about 20 hrs, preferably about 16 to 18 hrs. Other conditions which do not deviate radically from the ones described may also be utilized as an artisan would know.

The present method is applicable to the field of gene therapy, since it permits the introduction of genetic material encoding and regulating specific genetic traits. Thus, in the human, for example, by treating parents it is possible to correct many single gene disorders which otherwise might affect their children. It is similarly possible to alter the expression of fully inheritable disorders or those disorders having at least a partially inherited basis, which are caused by interaction of more than one gene, or those which are more prevalent because of the contribution of multiple genes. This technology may also be applied in a similar way to correct disorders in animals other than human primates. In some instances, it may be necessary to introduce one or more "gene(s)" into the germ cells of the animal to attain a desired therapeutic effect, as in the case where multiple genes are involved in the expression or suppression of a defined trait. In the human, examples of multigenic disorders include diabetes mellitus caused by deficient production of, or response to, insulin, inflammatory bowel disease, certain forms of atheromatus cardiovascular disease and hypertension, schizophrenia and some forms of chronic depressive disorders, among others. In some cases, one gene may encode an expressible product, whereas another gene encodes a regulatory function, as is known in the art. Other examples are those where homologous recombinant methods are applied to repair point mutations or deletions in the genome, inactivation of a gene causing pathogenesis or disease, or insertion of a gene that is expressed in a dominant negative manner, or alterations of regulating elements such as gene promoters, enhancers, the untranslated tail region of a gene, or regulation of expansion of repeated sequences of DNA which cause such diseases as Huntingdon's chorea, Fragile-X syndrome and the like.

A specific reproductive application of the present method is to the treatment of animals, particularly humans, with disorders of spermatogenesis. Defective spermatogenesis or spermiogenesis frequently has a genetic basis, that is, one or mutations in the genome may result in failure of production of normal sperm cells. This may happen at various stages of the development of germ cells, and may result in male infertility or sterility. The present invention is applicable, for example, to the insertion or incorporation of nucleic acid sequences into a recipient's genome and, thereby, establish spermatogenesis in the correction of oligozoospermia or azoospermia in the treatment of infertility. Similarly, the present methods are also applicable to males whose subfertility or sterility is due to a motility disorder with a genetic basis.

The present method is additionally applicable to the generation of transgenic animals expressing agents which are of therapeutic benefit for use in human and veterinary medicine or well being. Examples include the production of pharmaceuticals in domestic cows' milk, such as factors which enhance blood clotting for patients with types of haemophilia, or hormonal agents such as insulin and other peptide hormones.

The present method is further applicable to the generation of transgenic animals of a suitable anatomical and physiological phenotype for human xenograft transplantation. Transgenic technology permits the generation of animals which are immune-compatible with a human recipient. Appropriate organs, for example, may be removed from such animals to allow the transplantation of, for example, the heart, lung and kidney.

In addition, germ cells transfected in accordance with this invention may be extracted from the transgenic animal, and stored under conditions effective for later use, as is known in the art. Storage conditions include the use of cryopreservation using programmed freezing methods and/or the use of cryoprotectants, and the use of storage in substances such as liquid nitrogen. The germ cells may be obtained in the form of a male animal's semen, or separated spermatozoa, or immature spermatocytes, or whole biopsies of testicular tissue containing the primitive germ cells. Such storage techniques are particularly beneficial to young adult humans or children, undergoing oncological treatments for such diseases such as leukemia or Hodgkin's lymphoma. These treatments frequently irreversibly damage the testicle and, thus, render it unable to recommence spermatogenesis after therapy by, for example, irradiation or chemotherapy. The storage of germ cells and subsequent testicular transfer allows the restoration of fertility. In such circumstances, the transfer and manipulation of germ cells as taught in this invention are accomplished, but transfection is generally not relevant or needed.

In species other than humans, the present techniques are valuable for transport of gametes as frozen germ cells. Such transport will facilitate the establishment of various valued livestock or fowl, at a remote distance from the donor animal. This approach is also applicable to the preservation of endangered species across the globe.

The invention will now be described in greater detail by reference to the following non-limiting examples. The pertinent portions of the contents of all references, and published patent applications cited throughout this patent necessary for enablement purposes are hereby incorporated by reference.

EXAMPLES

TRANSFECTION OF MALE GERM CELLS IN VIVO

In Vivo Adenovirus-enhanced Transferrin-polylysine-mediated Delivery of Green Lantern Reporter Gene Delivery System to Testicular Cells The adenovirus enhanced transferrin-polylysine-mediated gene delivery system has been described and patented by Curiel al. (Curiel D. T., et al. Adenovirus enhancement of transferrin-polylysine-mediated gene delivery, PNAS USA 88: 8850–8854 (1991). The delivery of DNA depends upon endocytosis mediated by the transferrin receptor (Wagner et al., Transferrin-polycation conjugates as carriers for DNA uptake into cells, PNAS (USA) 87: 3410–3414 (1990). In addition this method relies on the capacity of adenoviruses to disrupt cell vesicles, such as endosomes and release the contents entrapped therein. This system can enhance the gene delivery to mammalian cells by as much as 2,000 fold over other methods.

The gene delivery system employed for the in vivo experiments was prepared as shown in examples below.

Example 1

Preparation of Transferrin-poly-L-Lysine Complexes

Human transferrin was conjugated to poly (L-lysine) using EDC (1-ethyl-3-(3-dimethyl aminopropyl carbodiimide hydrochloride) (Pierce), according to the method of Gabarek and Gergely (Gabarek & Gergely, Zero-length cross-linking procedure with the use of active esters, Analyt. Biochem 185: 131 (1990)). In this reaction, EDC reacts with a carboxyl group of human transferrin to form an amine-reactive intermediate. The activated protein was allowed to react with the poly (L-lysine) moiety for 2 hrs at room temperature, and the reaction was quenched by adding hydroxylamine to a final concentration of 10 mM. The conjugate was purified by gel filtration, and stored at −20° C.

Example 2

Preparation of DNA for In Vivo Trasfection

The Green Lantern-1 vector (Life Technologies, Gibco BRL, Gaithersberg, Md.) is a reporter construct used for monitoring gene transfection in mammalian cells. It consists of the gene encoding the Green Fluorescent Protein (GFP) driven by the cytomegalovirus (CMV) immediate early promoter. Downstream of the gene is a SV40 polyadenylation signal. Cells transfected with Green Lantern-1 fluoresce with a bright green light when illuminated with blue light. The excitation peak is 490 nm.

Example 3

Preparation of Adenoviral Particles

Adenovirus dI312, a replication-incompetent strain deleted in the Ela region, was propagated in the Ela trans-complementing cell line 293 as described by Jones and Shenk (Jones and Shenk, PNAS USA (1979) 79: 3665–3669). A large scale preparation of the virus was made using the method of Mittereder and Trapnell (Mittereder et al., "Evaluation of the concentration and bioactivity of adenovirus vectors for gene therapy", J. Urology, 70: 7498–7509 (1996)). The virion concentration was determined by UV spectroscopy, 1 absorbance unit being equivalent to 10 viral particles /ml. The purified virus was stored at −70° C.

Example 4

Formation of Transferrin-poly-L Lysine-DNA-Viral Complexes

6 μg transferrin-polylysine complex from Example 1 were mixed in $7.3\times10^7$ adenovirus d1312 particles prepared as in Example 3, and then mixed with 5 ug of the Green Lantern DNA construct of Example 2, and allowed to stand at room temperature for 1 hour. About 100 ul of the mixture were drawn up into a micropipette, drawn on a pipette puller, and slightly bent on a microforge. The filled micropipette was then attached to a picopump (Eppendorf), and the DNA complexes were delivered under continuous pressure, in vivo to mice as described in Example 6.

Controls were run following the same procedure, but omitting the transferrin-poly-lysine-DNA-viral complexes from the administered mixture.

Example 5

Comparison of Adenovirus-enhanced Transferrin-polylysine & Lipofectin Mediated Transfection Efficiency The conjugated adenovirus particle complexed with DNA were tested on CHO cells in vitro prior to in vivo testing. For these experiments a luciferase reporter gene was used due to the ease of quantifying luciferase activity. The expression construct consists of a reporter gene encoding luciferase, is driven by the CMV promoter (Invitrogen, Carlsbad, Calif. 92008). CHO cells were grown in Dulbecco's modified Eagle's medium (DMEM) with 10% fetal calf serum. For gene transfer experiments CHO cells were seeded into 6 cm tissue culture plates and grown to about 50% confluency ($5\times10^5$ cells). Prior to transfection the medium was aspirated and replaced with serum free DMEM. Cells were either transfected with transferrin-polylysine-DNA complexes or with lipofectin DNA aggregates. For the transferrin-polylysine mediated DNA transfer, the DNA-adenovirus complexes were added to the cells at a concentration of $0.05–3.2\times10_4$ adenovirus particles per cell. Plates were returned to the 5% $CO_2$ incubator for 1 hour at 37° C. After 1 hour 3 ml of complete media was added to the wells and the cells were allowed to incubate for 48 hours before harvesting. The cells were removed from the plate, counted and then lysed for measurement of luciferase activity.

For cells transfected by lipofectin, 1 μg of CMV-luciferase DNA was incubated with 17 μl of Lipofectin (Life Technologies). The DNA-lipofectin aggregates were added to the CHO cells and allowed to incubate at 37° C. at 5% $CO_2$ for 4 hours. Three mls of complete medium was added then to the cells and they were allowed to incubate for 48 hours. The cells were harvested, counted and lysed for luciferase activity. The luciferase activity was measured by a luminometer. The results obtained are shown in Table 1.

The data included in Table 1 below show that the adenovirus-enhanced transferrin-polylysine gene delivery system is 1,808 fold more efficient than lipofection for transfection of CHO cells.

TABLE 1

Comparison of Lipofection & Adenovirus Enhanced Transferrin-polylysine Transfection of CHO Cells

| Sample | Treatment | Luciferase Activity (RLU) |
|---|---|---|
| 1 | 1 × $10^7$ particles + 6 ug CMV-Luc | 486 |
| 2 | 2.5 × $10^7$ particles + 6 ug CMV-Luc | 1,201 |
| 3 | 5.0 × $10^7$ particles + 6 ug CMV-luc | 11,119 |
| 4 | 1 × $10^7$ particles + 6 ug CMV-Luc | 2,003,503 |
| 5 | Lipofection | 1,108 |
| 6 | Unmanipulated cells | 155 |

Example 6

In Vivo Delivery of DNA to Animal's Germ Cells via Tranferrin-L-lysine-DNA-Viral Complexes The GFP DNA-transferrin-polylysine viral complexes, prepared as described in Example 4 above, were delivered into the seminiferous tubules of three (3)-week-old B6D2F1 male mice. The DNA delivery by transferrin receptor-mediated endocytosis is described by Schmidt et al. and Wagner et al. (Schmidt et al., Cell 4: 41–51 (1986); Wagner, E., et al. PNAS (1990), (USA) 81: 3410–3414 (1990)). In addition, this delivery system relies on the capacity of adenoviruses to disrupt cell vesicles, such as endosomes and release the contents entrapped therein. The transfection efficiency of this system is almost 2,000 fold higher than lipofection.

The male mice were anesthetized with 2% Avertin (100% Avertin comprises 10 g 2,2,2-tribromoethanol (Aldrich) and 10 ml t-amyl alcohol (Sigma), and a small incision made in their skin and body wall, on the ventral side of the body at the level of the hind leg. The animal's testis was pulled out through the opening by grasping at the testis fat pad with forceps, and the vas efferens tubules exposed and supported by a glass syringe. The GFP DNA-transferrin-polylysine viral complexes were injected into a single vasa efferentia using a glass micropipette attached to a hand held glass syringe or a pressurized automatic pipettor (Eppendorf), and Trypan blue added to visualize the entry of the mixture into the seminiferous tubules. The testes were then placed back in the body cavity, the body wall was sutured, the skin closed with wound clips, and the animal allowed to recover on a warm pad.

Example 7

Detection of DNA and Transcribed Message

Nine (9) days after delivery of the genetic material to the animals' testis, two of the animals were sacrificed, their testes removed, cut in half, and frozen in liquid nitrogen. The DNA from one half of the tissues, and the RNA from the other half of the tissues were extracted and analyzed.

(a) Detection of DNA

The presence of GFP DNA in the extracts was tested 9 days after administration of the transfection mixture using the polymerase chain reaction, and GFP specific oligonucleotides. GFP DNA was present in the testes of the animals that had received the DNA complexes, but was absent from sham operated animals.

(b) Detection of RNA

The presence of GFP mRNA was assayed in the testes of experimental animals as follows. RNA was extracted from injected, and non-injected testes, and the presence of the GFP messages was detected using reverse transcriptase PCR (RTPCR) with GFP specific primers. The GFP message was present in the injected testes, but not in the control testes. Thus, the DNA detected above by PCR analysis is, in fact, episomal GFP DNA, or GFP DNA which has integrated into the chromosomes of the animal. The transfected gene was being expressed.

Example 8

Expression of Non-endogenous DNA

Two males, one having received an injection with the GFP transfection mixture and a control to whom only surgery was administered, were sacrificed 4 days after injection, and their testes excised, and fixed in 4% paraformaldehyde for 18 hours at 4° C. The fixed testis was then placed in 30% sucrose in PBS with 2 mM $MgCl_2$ for 18 hours at 4° C., embedded in OCT frozen on dry ice, and sectioned. When the testes of both animals were examined with a confocal microscope with fluorescent light at a wavelength of 488 nM, bright fluorescence was detected in the tubules of the GFP-injected mice, but not in the testes of the controls. Many cells within the seminferous tubules of the GFP-injected mouse showed bright fluorescence, which evidences that they were expressing Fluorescent Green Protein.

Example 9

Generation of Offspring from Normal Matings

GFP transfected males were mated with normal females. The females were allowed to complete gestation, and the pups to be born. The pups (F1 offspring or progeny) were screened for the presence of the novel genetic material(s).

Example 10

In Vitro Transfection of Testicular Cells in Vitro

Cells were isolated from the testes of three 10-day-old mice. The testes were decapsulated and the seminiferous tubules were teased apart and minced with sterile needles. The cells were incubated in enzyme mixture for 20 minutes at 37° C. The enzyme mixture was made up of 10 mg bovine serum albumin (embryo tested), 50 mg bovine pancreatic trypsin type III, Clostridium collagenase type I, 1 mg bovine pancreatic DNAse type I in 10 mls of modified HTF medium (Irvine Scientific, Irvine, Calif.). The enzymes were obtained from Sigma Company (St. Louis, Missouri 63178). After digestion, the cells were washed twice by centrifugation at 500×g with HTF medium and resuspended in 250 $\mu$l HTF medium. The cells were counted, and $0.5 \times 10^6$ cells were plated in a 60 mm culture dish in a total volume of 5ml DMEM (Gibco-BRL, Life Technologies, Gaithesburg, Md. 20884). A transfection mixture was prepared by mixing 5 $\mu$g Green Lantern DNA (Gibco-BRL, Life Technologies, Gaithesburg, Md. 20884) with 20 $\mu$l Superfect (Quagen, Santa Clarita, Calif. 91355) and 150 $\mu$l DMEM. The transfection mix was added to the cells and they were allowed to incubate for 3 hours at 37° C., 5% $CO_2$ The cells were transferred to a 33° C. incubator and incubated overnight.

The following morning the cells were assessed for transfection efficiency by counting the number of fluorescent cells. In this experiment the transfection efficiency was 90% (Figure not shown). The testicular cells transfected with Green Lantern viewed with Nomaski optics ×20 show the same cells viewed with FITC. Nearly all the cells were fluorescent, which is confirmation of their successful transfection.

The cells were injected into the testis via the vasa efferentia using a micropipette. $3 \times 10^5$ cells in a total volume of 50 $\mu$l were used for the injection. The cells were mixed with Trypan blue prior to the injection. Three adult mice were injected with transfected cells. The Balb/cByJ recipient mice had been irradiated 6 weeks prior to the injection with 800 Rads of gamma irradiation. One mouse became sick and was sacrificed 48 hours after the injection. The testes from this mouse were dissected, fixed and processed for histology.

The two remaining males were bred with normal females as shown. After 4 months pups were born. Litters are currently being screened for the integration of the transgene.

Example 11

Preparation of a Cell Suspension from Testicular Tissue for Cryopreservation

A cell suspension was prepared from mice of different ages as described below.

Group I: 7–10 day olds

Group II: 15–17 day olds

Group III: 24–26 day olds

The mice's testes were dissected, placed in phosphate buffered saline (PBS) decapsulated, and the seminiferous tubules were teased apart. Seminiferous tubules from groups I and II were transferred to HEPES buffered culture medium (D-MEM) (Gibco-BRL, Life Technologies, Gaithesburg, Md. 20884) containing 1 mg/ml Bovine serum albumin (BSA) (Sigma, St. Louis, Mo. 63178) and Collagenase Type I (Sigma) for the removal of interstitial cells. After a 10 minute incubation at 33° C., the tubules were lifted into fresh culture medium. This enzymatic digestion was not carried out on the testes from group I because of their fragility.

The tubules from group II and III mice or the whole tissue from group I mice were transferred to a Petri dish with culture medium and were cut into 0.1–1 mm pieces using a sterile scalpel and needle. The minced tissue was centrifuged at 500×g for 5 minutes and the pellet was resuspended in Iml of enzyme mix. The enzyme mix was made up in D-DMEM with HEPES (GibcoBRL) and consisted of lmg/ml bovine serum albumin (BSA) (Sigma, embryo tested), 1 mg/ml collagenase I (Sigma) and 5 mg/ml bovine pancreatic trypsin (Sigma) and 0.1 mg/ml deoxyribonuclease I (DN-EP, Sigma). The tubules were incubated in enzyme mix for 30 minutes at 33° C. After the incubation, 1 ml of medium was added to the mix and the cells were centrifuged at 500×g for 5 min. The cells were washed twice in medium by centrifugation and resuspension. After the final wash the cell pellet was resuspended in 250 μl of culture medium and counted.

Example 12

Cryopreservation of Methods for Testicular Cells (a) Propanediol (PROH)-sucrose Method Testicular cells from a total of 31 mice (age 8–12 weeks) were cryopreserved using 6 different freezing and thawing protocols. In addition to freezing cell supsensions, pieces of testicular tissue were frozen (see freezing method above). The cell suspension was prepared as described above.

The cell suspension was incubated in a buffer stock solution consisting of 80% phosphate buffered saline (PBS) and 20% human serum (SPR, Helsinki, Finland) for 5 minutes. The cells were then incubated in 1.5M PROH for 10 minutes, pelleted by centrifngation and resuspended in 1.5M PROH with 0.1M sucrose. The cell suspension was loaded into straws (0.25 μm, Paillette, L'Aigle, France) or 1 ml cryogenic vials (Nunc cryotube). Samples were frozen in a controlled temperature freezing machine (Planer Kryo, Series III, Planer Biomed, Sunbury on Thames, UK). The samples were cooled at a rate of 2° C./min to −8° C., and seeded manually using forceps cooled in liquid nitrogen. After 10 min the samples were cooled at 0.3° C./min to −30° C. after which they were cooled at a rate of −50° C./min to −150° C. Samples were then stored in liquid nitrogen at −196° C.

The samples were removed from liquid nitrogen and kept at room temperature for 2 min. The samples were incubated in 1M PROH+0.1M sucrose for 5 min, followed by an incubation in 0.5M PROH+0.1M sucrose for 5 min and then in 0.1M sucrose for 10 min. The cell suspension was placed in buffer stock.

(b) Glycerol Yolk Buffer Method

The cell suspension was pipetted into a vial and the yolk buffer freezing medium (Irvine Scientific, Santa Ana, Calif.) was added drop by drop to make up approximately 50% of the total volume. The samples were cooled in a controlled freezer at an initial cooling rate of 0.5° C./min to a temperature of 1.5° C. The samples were then cooled at 10° C./min until they reached a temperature of −80° C. On reaching this temperature the samples were placed in liquid nitrogen for storage.

Samples were removed from liquid nitrogen and thawed at room temperature. The suspension was centrifuged and the pelleted cells were resuspended in PBS.

(c) DMSO Method

Cells were pipetted into a cryogenic vial containing 60% medium 199 with Earle's salts (Gibco, Gaithesburg, Md.), 20% human AB serum. 20% DMSO was added to the cells drop by drop to make up 50% of the total volume. The cells were cooled at a rate of 4° C./min to 0° C. and then at 1° C./min to −80° C., then at 10° C./min to −100° C. and finally at 20° C./min to −160° C. The samples were then stored in liquid nitrogen.

Samples were removed from liquid nitrogen and thawed at room temperature. The suspension was centrifuged and the pelleted cells were resuspended in PBS.

(d) DMSO-Heparin Method

Cells were pipetted into a cryogenic vial. A solution containing 45% 5000 U/ml heparin (Tovens medicinske fabrik, Ballerup, Derunark), 15% DMSO and 40% albumin (SPR) in PBS was added drop by drop to make up 50% of the total volume. The freezing and thawing programme was the same as that used for the glycerol yolk buffer method.

(e) Quick DMSO method

Cells were pipetted into a cryogenic vial and a freezing solution containing 90% fetal calf serum and 10% DMSO was added at room temperature to make up 90% of the total volume. The samples were placed in a −70° C. freezer (Revco Scientific Corp., Asheville, N.C.) for 24 hours. The samples were then stored in liquid nitrogen. The thawing procedure was that same as that used for the Glycerol yolk method.

(f) Quick Glycerol Method

The cells were pipetted into a cryogenic vial and a freezing solution containing 70% DMEM, 20% fetal calf serum and 10% filtered glycerol was added to the cells to make up 90% of the total volume. The resuspension was incubated at 37° C. for 10 min. The samples were placed in a −70° C. freezer for 24 hours after which they were stored in liquid nitrogen.

The thawing procedure was the same as that described for the Glycerol yolk method.

(g) Freezing Testicular Tissue

The method used for freezing whole testicular tissue was the same as the method we described previously for freezing ovarian tissue (Hovatta, et al., Human Reprod. 11: 1268–1272 (1996). The testicles of 6 mice were decapsulated in culture medium (D-MEM) and cut into 0.3–1.0 mm pieces. The tissue pieces were placed in medium containing 1.5M PROH in PBS with 20% serum for 10 min. at room temperature. They were transferred to cyrogenic vials and cooled at 2° C./min to −8° C. The vials were seeded manually with forceps dipped in liquid nitrogen. After 10 min the cooling was continued at a rate of 0.3° C./min to −30° C. and then at a rate of 50° C./min to −150° C. When the samples reached this temperature they were transferred to liquid nitrogen.

The vials were removed from the liquid nitrogen and allowed to come to room temperature for 2 min. They were then placed in a water bath at 30° C. until they had thawed. The tissue pieces were transferred to a Petri dish containing 1.0M PROH, 0.1M sucrose and 20% serum in PBS for 5 min. They were then transferred to a solution containing 0.5M PROH, 0.1M sucrose and 20% serum in PBS for 5 min and then to a solution containing 0.1M sucrose with 20% serum in PBS for 10 min. The cells were kept in culture medium.

The results obtained from the above experimental procedures are summarized in Table 2 below.

TABLE 2

Comparison of Results by Different Methods

| Method | Cell Viability after Freeze/Thaw |
|---|---|
| Propanediol-Sucrose | 63% |
| Glyerol-Yolk Buffer | 56% |
| DMSO | 50% |
| Quick DMSO | 33% |
| DMSO-Heparin | 23% |
| Quick-Glycerol | 13% |

From Table 2 above, it may be seen that the testicular cells that had been frozen using the propanediol-sucrose method had the highest percentage of viable cells upon thawing than cells frozen using the other methods. The propanediol-sucrose freezing method was significantly less damaging to testicular cells than the DMSO method used by Avarbock et al., 1996 for freezing testicular cells prior to transfer. The propanediol-sucrose method was also shown to be good for freezing human ovarian tissue as described by Hovatta et al. (Hovatta et al., Human Reprod. 11: 1268–1272 (1996a), the relevant part of which is incorporated herein by reference, and pieces of testicular tissue.

The testicular spermatozoa from a human biopsy were frozen-thawed using the glycerol-yolk buffer method, and then used for intracytoplasmic injection of eggs (ICSI). A successful pregnancy resulted (Hovatta, O. et al., Pregnancy resulting from intracytoplasmic injection of spermatozoa from a frozen thawed testicular biopsy, Human Reprod. 11: 2472–2473 (1996b).

What is claimed is:

1. An in vivo method of incorporating a polynucleotide into germ cells of a male non-human mammal for the production of transgenic non-human mammals, comprising:

administering by injection into a testis of a male non-human mammal a transfection mixture comprising at least one polynucleotide encoding a gene product in operable linkage with a promoter, and at least one transfecting agent, other than a liposome/DNA complex, wherein said testis contains the germ cells of the male non-human mammal, and wherein said germ cells are selected from the group consisting of spermatogonial stem cells, type B spermatogonia, primary spermatocytes, preleptotene spermatocytes, leptotene spermatocytes, zygotene spermatocytes, pachytene spermatocytes, secondary spermatocytes, spermatids, and spermatozoa; and allowing the polynucleotide encoding a gene product to be taken up by, and released into, the germ cells so that the released polynucleotide is incorporated into the genome of the germ cells of said male non-human mammal thereby producing a transgenic non-human mammal.

2. The method of claim 1, wherein the transfecting agent comprises a viral vector selected from the group consisting of a retroviral vector, an adenoviral vector, a mumps viral vector, a virus-derived DNA vector sequence, and a mixture of the vectors thereof, wherein said transfecting agent facilitates uptake and release of the polynucleotide into the cytoplasm of the germ cells.

3. The method of claim 2, wherein the viral vector is a transferrin-polylysine enhanced adenoviral vector or a lentiviral vector.

4. The method of claim 3, wherein the lentiviral vector is a human immunodeficiency virus vector.

5. The method of claim 2, wherein the viral vector is a Moloney murine leukemia virus-derived vector.

6. The method of claim 1, wherein the transfecting agent comprises an adenovirus vector having endosomal lytic activity, and wherein the gene product is expressed in the germ cells.

7. An in vivo method of incorporating a polynucleotide into germ cells of a male non-human mammal for the production of transgenic non-human mammals, comprising:

administering by injection into a testis of a male non-human mammal a transfection mixture comprising a transferrin-polylysine enhanced adenoviral vector complexed with at least one polynucleotide encoding a gene product in operable linkage with a promoter, wherein said testis contains the germ cells of the male non-human mammal, and wherein said germ cells are selected from the group consisting of spermatogonial stem cells, type B spermatogonia, primary spermatocytes, preleptotene spermatocytes, leptotene spermatocytes, zygotene spermatocytes, pachytene spermatocytes, secondary spermatocytes, spermatids, and spermatozoa; and allowing the adenoviral vector to be taken up by, and released into, the germ cells so that the polynucleotide is incorporated into the genome of the germ cells of said male non-human mammal thereby producing a transgenic non-human mammal.

8. The method according to claim 1 or claim 7, wherein the transfection mixture further comprises a male-germ-cell-targeting molecule consisting of a c-kit ligand.

9. The method of claim 1 or claim 7, wherein the promoter is selected from the group consisting of a c-kit promoter, a b-Myb promoter, a c-raf-1 promoter, an ATM (ataxia-telangiectasia) promoter, an RBM (ribosome binding motif) promoter, a DAZ (deleted in azoospermia) promoter, an XRCC-1 promoter, an HSP 90 (heat shock gene) promoter, and a FRM1 (from fragile X site) promoter.

10. The method according to claim 1 or claim 7, wherein the transfection mixture further comprises an immunosuppressing agent.

11. The method of claim 10, wherein the immunosuppressing agent is selected from the group consisting of cyclosporin and a corticosteroid .

12. The method according to claim 1 or claim 7, wherein the injection is a percutaneous injection.

13. The method according to claim 1 or claim 7, wherein the injection of the transfection mixture is into the vas efferens of the testis.

14. The method according to claim 1 or claim 7, wherein the injection of the transfection mixture is into the seminiferous tubule of the testis.

15. The method according to claim 1 or claim 7, wherein the injection of the transfection mixture is into the rete of the testis.

16. Tihe method according to claim 1 or claim 7, wherein the non-human mammal is selected front the group consisting of non-human primate, farm mammal, and marine mammal.

17. A method of isolating or selecting a male germ cell transfected with at least one polynucleotide encoding a gene product and at least one genetic selection marker, comprising performing the method of claim 1 or claim 7, wherein the transfection mixture further comprises at least one genetic selection marker; and isolating, or selecting a transfected male germ cell by detection of the genetic selection marker.

18. A method of transferring male germ cells transfected with at least one polynucleotide encoding a gene product to a testis of a recipient male non-human mammal for the production of transgenic non-human mammals, comprising:

isolating or selecting male germ cells whose genomes comprise at least one polynucleotide encoding a gene product and at least one polynucleotide encoding a genetic selection marker, wherein the germ cells are isolated or selected by the method of claim 17, and wherein the germ cells a from a donor male non-human mammal;

administering the isolated or selected germ cells to a testis of a recipient male non-human mammal; and allowing, the administered germ cells to lodge in a seminiferous tubule of the recipient male non-human maiinmal thereby producing a male non-human mammal useful for producing a transgenic non-human mammal.

19. The method of claim 18, wherein the method further comprises co-administering Leydig or Sertoli cells to the testis with the isolated or selected germ cells.

20. The method of claim 18, wherein the method further comprises isolating or selecting translected Leydig or Sertoli cells, and co-administering to the testis with the isolated or selected germ cells.

21. The method of claim 18, wherein the polynucleotide encoding the gene product is derived from the same species of non-human mammal as the recipient non-human mammal.

22. The method of claim 18, wherein the polynucleotide encoding the gene product is derived from a human.

23. The method of transferring autologous male germ cells and Leydig cells and/or Sertoli cells to the tes! is of a non-human mammal, comprising performing the method of claim 18, wherein the dolor non-human mammal is the same as the recipient non-human mammal and autologous Leydig cells and/or Sertoli cells are co-administered with the male germ cells.

24. The method of claim 18, wherein the donor non-human mammal is the same as the recipient non-human mammal.

25. The method according to claim 1 or claim 7, wherein the polynucleotide encoding a gene product is expressed in the germ cells.

* * * * *

UNITED STATES PATENT AND TRADEMARK OFFICE

CERTIFICATE OF CORRECTION

PATENT NO. : 6,316,692 B1
DATED : November 13, 2001
INVENTOR(S) : Carol W. Readhead and Robert Winston It is certified that error appears in the above-identified patent and that said Letters Patent is hereby corrected as shown below:

Title page,
Item [73], please insert -- Assignees: Cedars-Sinai Medical Center
Los Angeles, California, and
Imperial College of Science, Technology and Medicine
South Kensington, London, UK --

Column 18,
Line 64, please delete "Tihe" and insert therefor -- The --.
Line 65, please delete "front" and insert therefor -- from --.

Column 19,
Line 8, please delete "," after the word isolating.
Line 20, please delete "a" and insert therefor -- are --.
Line 24, please delete "," after the word allowing.
Line 26, please delete "maiinmal" and insert therefor -- mammal --.

Column 20,
Line 5, please delete "translected" and insert therefor -- transfected --.
Line 14, please delete "The" and insert therefor -- A --.
Line 15, please delete "tes! is" and insert therefor -- testis --.
Line 17, please delete "dolor" and insert therefor -- donor --.

Signed and Sealed this

Fifth Day of November, 2002

*Attest:*

JAMES E. ROGAN

*Attesting Officer*

*Director of the United States Patent and Trademark Office*

UNITED STATES PATENT AND TRADEMARK OFFICE

CERTIFICATE OF CORRECTION

PATENT NO. : 6,316,692 B1
DATED : November 13, 2001
INVENTOR(S) : Carol W. Readhead and Robert Winston It is certified that error appears in the above-identified patent and that said Letters Patent is hereby corrected as shown below:

Column 1,
Line 8, before "BACKGROUND OF THE INVENTION", please insert the following paragraph:
-- The U.S. Government has paid-up license in this invention and the right in limited circumstances to require the patent owner to license others on reasonable terms as provided for by the terms of NIH Grant No. RO1 RR12406. --.

Signed and Sealed this

Thirtieth Day of September, 2003

JAMES E. ROGAN
*Director of the United States Patent and Trademark Office*